United States Patent [19]

Siriwardane

[11] Patent Number: 5,177,294
[45] Date of Patent: Jan. 5, 1993

[54] CATALYSTS FOR CONVERSION OF METHANE TO HIGHER HYDROCARBONS

[75] Inventor: Ranjani V. Siriwardane, Morgantown, W. Va.

[73] Assignee: The United States of America as represented by the United States Department of Energy, Washington, D.C.

[21] Appl. No.: 700,290

[22] Filed: May 15, 1991

[51] Int. Cl.$^5$ .............................................. C07C 2/00
[52] U.S. Cl. .................................. 585/658; 585/661; 585/700
[58] Field of Search ................................ 585/658, 661

[56] References Cited

U.S. PATENT DOCUMENTS 4,499,322  2/1985  Jones et al. ........................ 585/500
4,886,932  12/1989  Leyshon .............................. 585/500

FOREIGN PATENT DOCUMENTS 0189079  7/1986  European Pat. Off.
156842A  10/1985  United Kingdom

OTHER PUBLICATIONS

Kiyoshi Otsuka et al., "Active and selective Catalysts for the Synthesis of $C_2H_2$ and $C_2H_6$ via Oxidative Coupling of Methane", Journal of Catalysts 100 pp. 353-359 1986.

C. Andrew Jones et al., "The Oxidative Conversion of Methane to Higher Hydrocarbons over Alkali-Promoted Mn/SiO$_2$", Journal of Catalysts 103, pp. 311-319 1987.

Tomoyasu Ito et al., "Oxidative Dimerization of Methane over a Lithium Promoted Magnesium Catalyst", Journal of American Chemical Society 107 pp. 5062-5068 1985.

*Primary Examiner*—Asok Pal
*Assistant Examiner*—P. Achutamurthy
*Attorney, Agent, or Firm*—David E. Breeden; Stephen D. Hamel; William R. Moser

[57] ABSTRACT

Catalysts for converting methane to higher hydrocarbons such as ethane and ethylene in the presence of oxygen at temperatures in the range of about 700° to 900° C. are described. These catalysts comprise calcium oxide or gadolinium oxide respectively promoted with about 0.025-0.4 mole and about 0.1-0.7 mole sodium pyrophosphate. A preferred reaction temperature in a range of about 800° to 850° C. with a preferred oxygen-to-methane ratio of about 2:1 provides an essentially constant $C_2$ hydrocarbon yield in the range of about 12 to 19 percent over a period of time greater than about 20 hours.

8 Claims, 4 Drawing Sheets

CATALYSTS FOR CONVERSION OF METHANE TO HIGHER HYDROCARBONS

The United States Government has rights in this invention pursuant to the employer-employee relationship of the U.S. Department of Energy and the inventor.

BACKGROUND OF THE INVENTION

The present invention relates generally to the conversion of methane to $C_2$ hydrocarbons such as ethane and ethylene by a catalytic oxidation reaction, and more particularly to the catalysts for such a reaction which comprise sodium pyrophosphate over either calcium oxide or gadolinium oxide and which are each capable of providing high yields of ethane and ethylene over relatively long periods of reaction.

Methane is known for its value as a fuel and is a major component of natural gas. While the exploitation of natural gas resources provides a major energy source, the transportation of natural gas in quantity from relatively remote resources requires the use of extensive and sophisticated pipe line systems which present considerable expenditures and give rise to some problems in such transportation of natural gas. In order to reduce these expenditures and problems, investigations have been conducted in an effort to convert the methane in the natural gas to products which can be more readily managed and/or transported than natural gas. The high molecular stability of the methane molecule makes it difficult to convert the methane to other chemical products such as the $C_2$ hydrocarbons of ethane and ethylene. Previous efforts in this area includes the use of oxidative coupling reactions which have successfully converted the methane to higher $C_2$ hydrocarbons so as to provide gaseous products which could be readily converted to liquid fuels and/or other desirable chemicals. While various metal oxide catalysts have been used to provide relatively high yields of $C_2$ hydrocarbons at satisfactory high conversion rates it was found that the reactivity of these previously known catalysts decreased fairly rapidly with time. For example, a lithium/magnesium catalyst which was capable of initially providing a yield of $C_2$ hydrocarbons ranging from 16 to 19 percent suffered a significant decrease in the order of about 25 percent in this relatively high conversion rate during the first 16 hours of its use.

SUMMARY OF THE INVENTION

Accordingly, it is the primary aim or objective of the present invention to provide catalysts for the selective conversion of methane to form higher hydrocarbons and which provide yields in such hydrocarbons at least comparable to those attainable by using previously known catalysts and yet which will remain essentially fully effective for periods of time significantly longer than provided by the previously known catalysts. Generally, the catalysts of the present invention facilitate the partial oxidation of methane to $C_2$ hydrocarbons of ethane and ethylene in the presence of oxygen at an elevated temperature. These catalysts comprise calcium oxide (CaO) or gadolinium oxide ($Gd_2O_3$) each promoted with sodium pyrophosphate ($Na_4P_2O_7$). When the catalyst is sodium pyrophosphate over calcium oxide, the sodium pyrophosphate content is in the range of about 0.025 to 0.4 mole per mole of calcium oxide. When the catalyst is sodium pyrophosphate over gadolinium oxide the sodium pyrophosphate content is in the range of about 0.1 to 0.7 mole per mole of gadolinium oxide. The catalyst of either sodium pyrophosphate over calcium oxide or sodium pyrophosphate over gadolinium oxide is heated and then contacted with a stream of gases comprising methane and oxygen for a duration sufficient to provide the $C_2$ hydrocarbon yield in the range of about 12 to 19 percent. In this reaction the methane to oxygen ratio in the stream of gases is in the range of about 1:1 to about 5:1, the catalyst is heated to a temperature in the range of about 700. to about 900° C. (923°–1173° K.), and the stream of gases are at a flow rate which will provide the sufficient duration of contact between the gases and the catalyst necessary to effect the desired yield of $C_2$ hydrocarbons.

Other and further objects of the present invention will become obvious upon an understanding of the embodiments and method about to be described or will be indicated in the appended claims, and various advantages not referred to herein will occur to one skilled in the art upon employment of the invention in practice.

Figure 1:
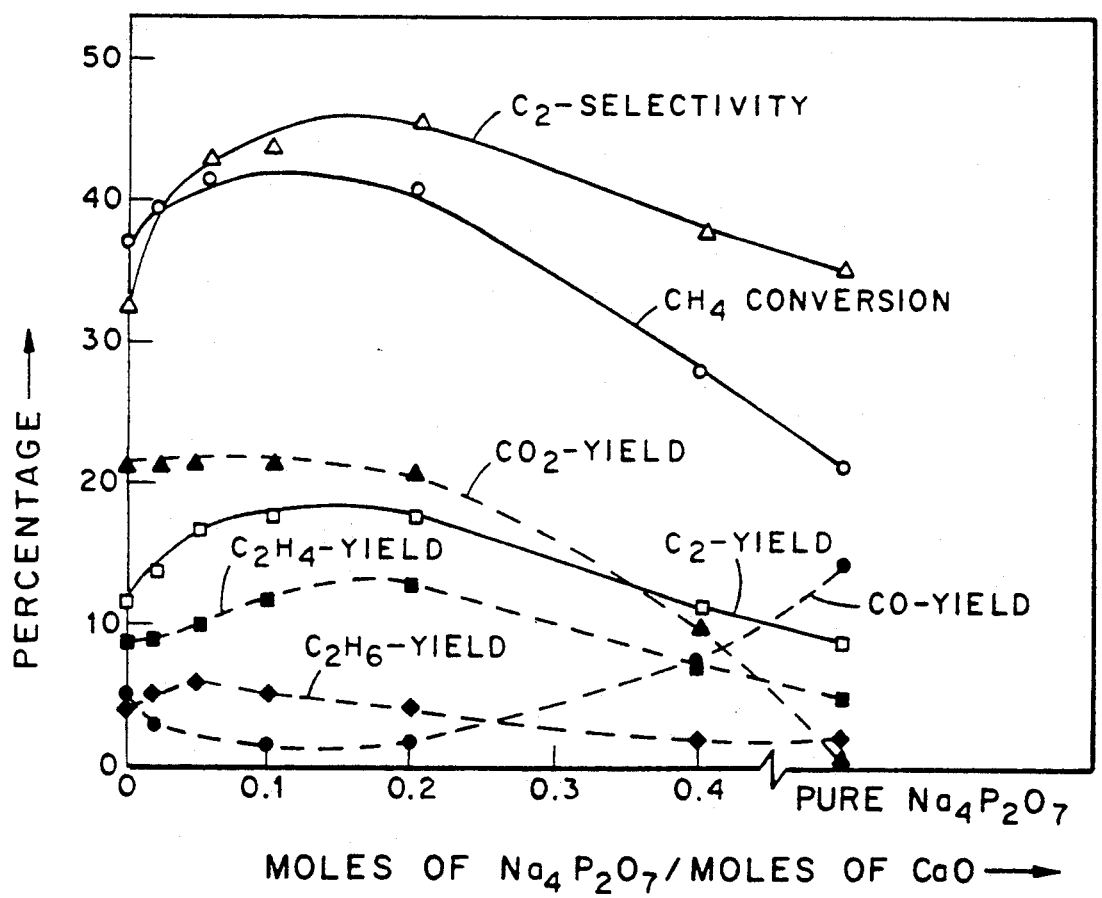
FIG. 1 is a graph illustrating the effect of the sodium concentration on the catalyst $Na_4P_2O_7/CaO$ at 828° C. (1101° K.)

Graphs showing preferred embodiments of the invention have been chosen for the purpose of illustration and description. The graphs are not intended to be exhaustive nor to limit the invention to the precise forms shown. The graphs are chosen and described in order to best explain the principles of the invention and their application and practical use to thereby enable others skilled in the art to best utilize the invention in various embodiments and modifications as are best adapted to the particular use contemplated.

DETAILED DESCRIPTION OF THE INVENTION

As briefly described above, the present invention relates to the selective catalytic conversion of methane to higher hydrocarbons of ethane and ethylene. The present invention is directed to the oxidative coupling of methane over calcium oxide or gadolinium oxide each promoted with sodium pyrophosphate. Calcium oxide and gadolinium oxide when promoted with sodium pyrophosphate are each found to provide an active and selective catalyst which is particularly suitable for the partial oxidation of methane to ethane and ethylene in the presence of oxygen at a temperature up to about 900° C. Yields of $C_2$ hydrocarbons in the range of about 12 to 19 percent are obtained by selectively varying the mole ratio of the sodium pyrophosphate to the calcium oxide or the gadolinium oxide, the reaction temperatures, and the methane-to-oxygen ratios. Preferably, the yields obtained over $Na_4P_2O_7/CaO$ are in the range of about 18 to 19 percent while the yields obtained over $Na_4P_2O_7/Gd_2O_3$ are in the range of about 17 to 18 percent. The ratios of methane to oxygen are in the range of about 5:1 to 2:1, the reaction temperatures are in the range of about 700° to 900° C., and the molecular ratio of the $Na_4P_2O_7$ to the CaO or the $Gd_2O_3$ is in the range of about 0.025 to 0.4 mole $Na_4P_2O_7$ per mole of CaO and about 0.1 to 0.7 mole of $Na_4P_2O_7$ per mole of $Gd_2O_3$. Preferably, in order to obtain the maximum $C_2$ yields, the methane-to-oxygen ratio is about 2:1, the reaction temperature is about 800°–850° C. for each of these catalysts, and the molecular ratio of the $Na_4P_2O_7$ to the CaO and $Gd_2O_3$ is about 0.1 to 0.2 mole $Na_4P_2O_7$ per mole of CaO and about 0.5 mole $Na_4P_2O_7$ per mole of $Gd_2O_3$.

The preparation of the catalysts can be achieved in any suitable manner. For example, the calcium oxide can be prepared by the decomposition of calcium acetate at 850° C. for a duration of 16 to 19 hours. The calcium oxide and sodium pyrophosphate were combined and added to ionized water and heated slowly while stirring until essentially all the water was evaporated to provide a thick paste which was then heated at 500° C. for a period of 16 hours followed by a 2 hour heating period at 700° C. The sodium pyrophosphate on gadolinium oxide was prepared in a similar manner in that the gadolinium oxide was first prepared by heating gadolinium nitrate in an oven at 850° C. for a period of 16 hours. The resulting gadolinium oxide was then promoted with sodium pyrophosphate by employing the same technique as utilized for promoting the calcium oxide.

The catalysts formed of calcium oxide or gadolinium oxide each promoted with sodium pyrophosphate were separately tested for methane conversion efficiency in a fixed-bed reactor operating at a pressure of one atmosphere and heated to the reaction temperature by resistively heating. Of course, in a commercial application any suitable type flow-type reactor heated by any desirable mechanism may be readily utilized. The test reactor used to determine the conversion efficiency of the catalysts was a high purity quartz tube having a length of 23.3 centimeters, a diameter of 4.5 millimeters, and containing a heated zone 9 centimeters in length. The catalysts were each tested separately by placing 0.25 gram weight of each catalyst (28 to 48 mesh) within the heating zone of the reactor and heating the catalyst to the desired reaction temperature in the range of about 700°–900° C. A mixture of methane and oxygen were then introduced into the reactor at various flow rates to determine the conversion efficiency. In the present experiments the reacting gas mixtures of methane and oxygen were diluted with helium to achieve a total of pressure of one atmosphere. In a field operation the methane and oxygen will normally be utilized without the addition of a diluting gas. Further, for commercial applications the reaction could proceed at reactor operating pressures greater than one atmosphere. When the catalyst was heated to the desired reaction temperature, the reacting gas mixtures were introduced into the reactor with the gases emerging from the reactor being analyzed in chromatograph columns which were connected to a conventional thermal conductivity detector. The conversion yield in mole percent was obtained by multiplying the selectivity for each carbon-containing product and the total methane conversion based on mole percent.

Figure 2:
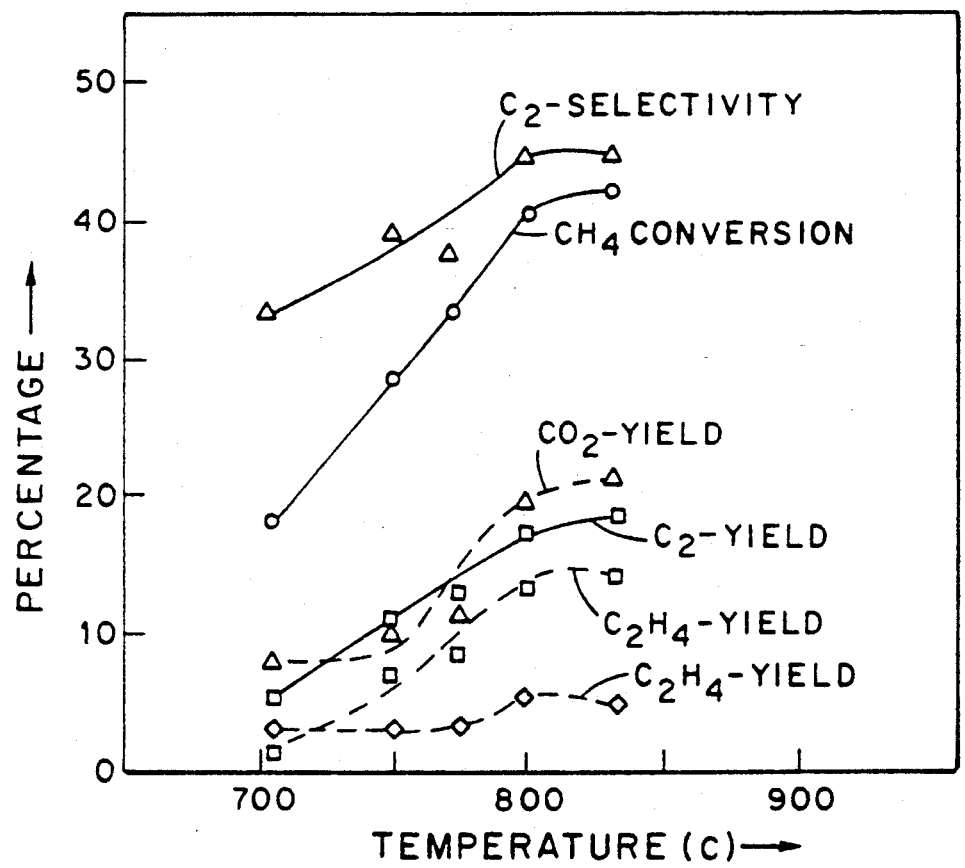
FIG. 2 is a graph showing the effect of temperature on the catalyst 0.1 $Na_4P_2O_7/CaO$.
Figure 3:
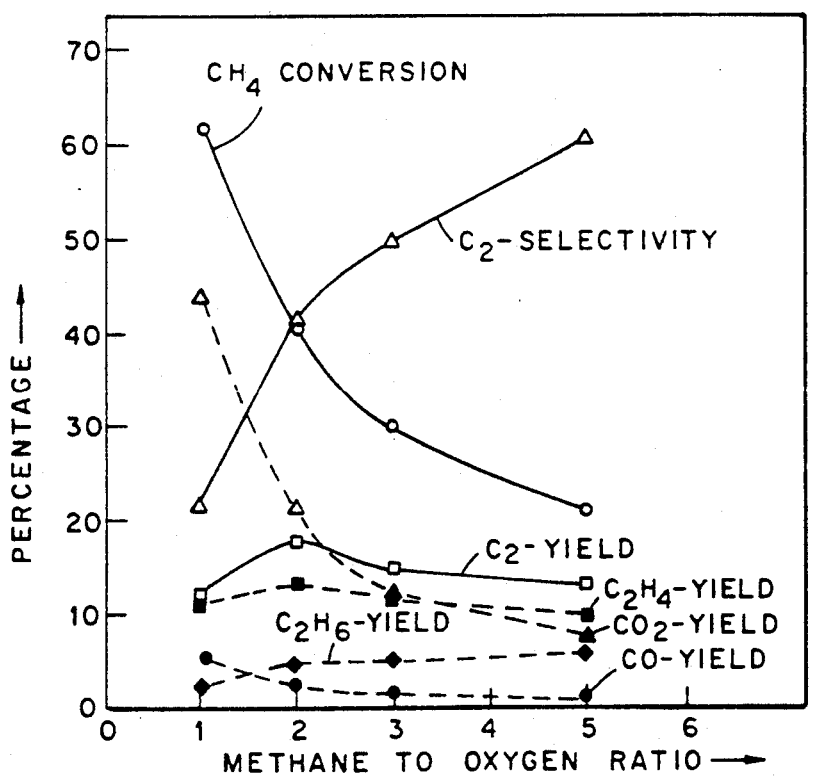
FIG. 3 is a graph illustrating the effect of methane-to-oxygen ratio on the catalyst 0.1 $Na_4P_2O_7/CaO$ at 828° C.

As shown in FIGS. 1–3, various yields of $C_2$ hydrocarbons on the $Na_4P_2O_7$/CaO catalyst were obtained by varying reaction parameters such as the sodium concentration, temperature, and ratio of the methane to the oxygen when using a total flow rate of methane and oxygen of about 31.5 ml/min. The flow rates of the methane and oxygen as used in these and other tests of the catalysts of the present invention are used merely for experimental purposes since under actual conditions in a commercial operation the flow rates will depend on several factors including reactor size and construction, temperature of the gases, and the concentration and location of the catalyst in the reactor. In any event, the flow rate of the methane and oxygen over the catalyst can be readily selected to assure that the contact of these gases with the catalyst is of a sufficient duration to provide the desired yield of $C_2$ hydrocarbons. As illustrated in FIG. 1, by varying the molecular ratio of the sodium ($Na_4P_2O_7$) in the range of about 0.025 to about 0.4 mole per mole of CaO at 828 C while using a methane to oxygen ratio of 2:1 that $C_2$ yields in a range of about 12 to 19 percent could be obtained with the preferred yield of about 18 to 19 percent occurring with a $Na_2P_2O_7$ concentration of about 0.1 to about 0.2 mole. As shown in FIG. 1, this catalyst when at a reaction temperature of 828° C. converts greater than about 30 percent of the methane to other gases while the selectivity to $C_2$ hydrocarbons is greater than about 33 percent. FIG. 2 shows that satisfactory yields of about 12 to about 19 percent $C_2$ hydrocarbons can be achieved with reaction temperatures in the range of about 750 to about 900° C. with the preferred yields of about 18 to 19 percent being achieved at a reaction temperature in the range of about 800° to 850° C. As shown in FIG. 3, the varying of the methane-to-oxygen ratios from about 5:1 to 1:1 provides various changes in the yield of the $C_2$ hydrocarbons with the preferred yield about 18 to 19 percent occurring with a methane-to-oxygen ratio of about 2:1. With the reactor heated to 828° C. and using methane-to-oxygen ratios of 2:1 and 5:1, the $C_2$ yield and product distribution for ethane, ethylene, carbon dioxide, and carbon monoxide remained essentially the same during a 26 hour test period on the 0.1 $Na_4P_2O_7$/CaO catalyst.

Figure 5:
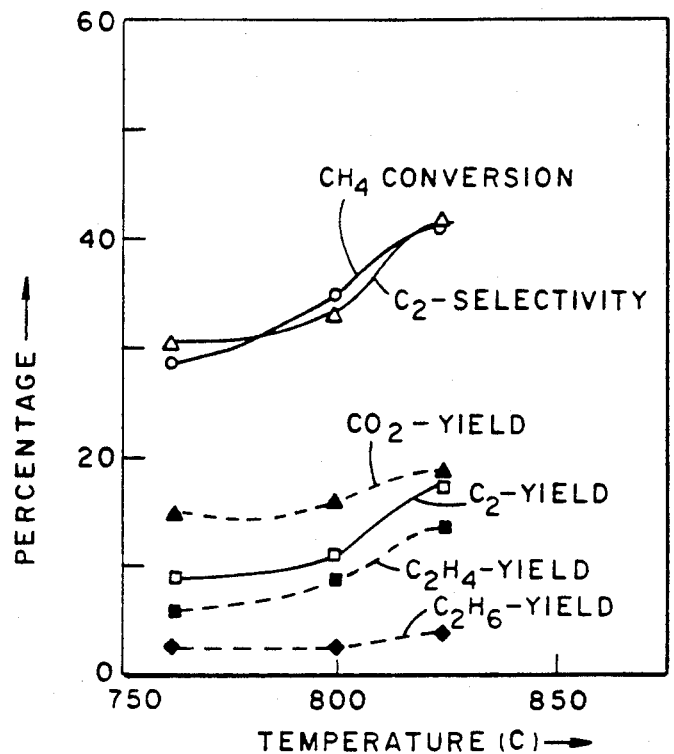
FIG. 5 is a graph showing the effect of temperature on the catalyst 0.1 $Na_4P_2O_7/Gd_2O_3$.
Figure 4:
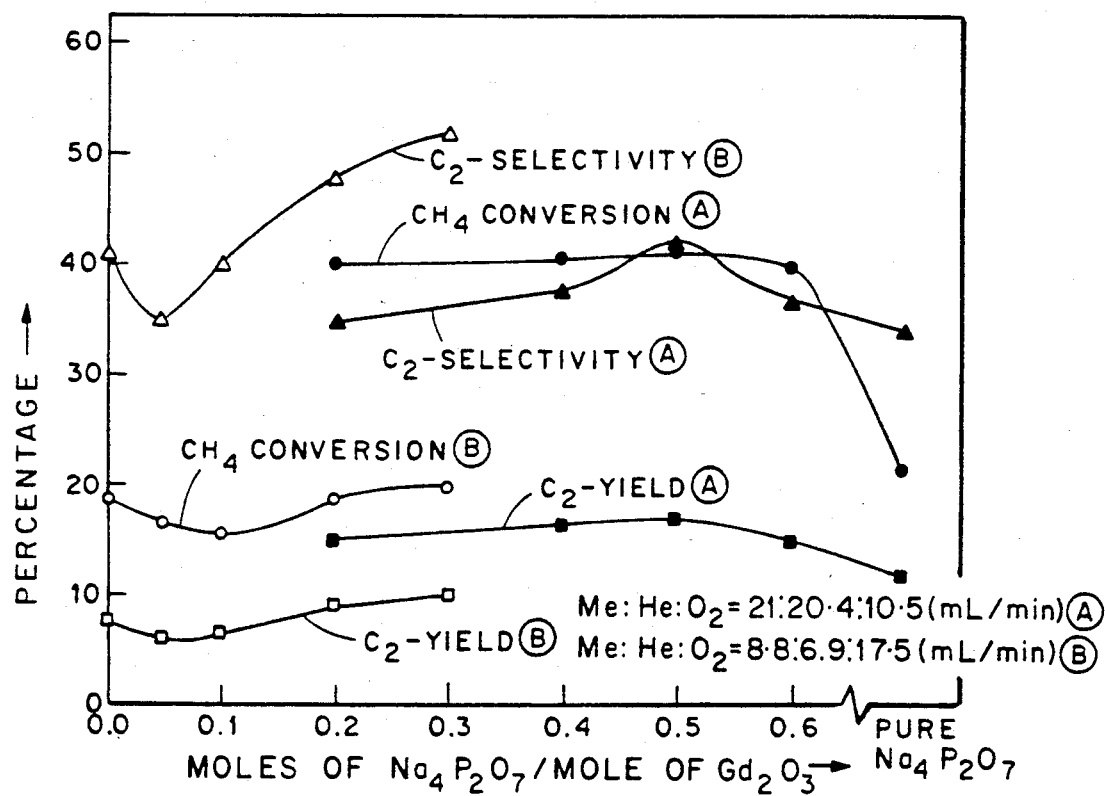
FIG. 4 is a graph illustrating the effect of sodium concentration on the catalyst $Na_4P_2O_7/Gd_2O_3$ at 828° C.

As shown in FIG. 4, the sodium concentration in the catalyst $Na_4P_2O_7$/$Gd_2O_3$ at 828° C. provided some differences in the yields of $C_2$ that were obtained by using the gaseous mixtures of methane, helium, and oxygen at two different ratios and flow rates of 21:20.4.10.5 ml/min and 8.8:6.9:17.5 ml/min, respectively. As shown, with the $Na_4P_2O_7$ providing up to about 0.1 mole $Na_4P_2O_7$/$Gd_2O_3$ of the catalyst there was a decrease in $C_2$ selectivity, $CH_4$ total conversion and $C_2$ yield but when the concentration of $Na_4P_2O_7$ was in the range of about 0.1 to 0.7 mole, satisfactory $C_2$ yields in the range of about 12 to about 18 percent were obtained. A preferred $C_2$ yield of about 17 to 18 percent was obtained with the $Na_4P_2O_7$ in a concentration of about 0.5 mole at a methane-to-oxygen ratio of about 2:1. As shown in FIG. 5, the temperature effect on the catalyst was demonstrated using a 0.1 $Na_4P_2O_7$/$Gd_2O_3$ mole concentration of the catalyst at temperatures in the range of about 750. to 850° C. with the highest $C_2$ yields being obtained at a reaction temperature in the range of about 800° to 850° C. This catalyst at 828° C. when at a methane-to-oxygen ratio of about 2:1 and having a $Na_4P_2O_7$ content between about 0 1 to 0.6 mole provided a methane conversion of about 40 percent with $C_2$ selectivity of greater than 33 percent.

In optimizing the reaction conditions to obtain the maximum $C_2$ yield over the catalyst $Na_4P_2O_7$/CaO, it was found that by increasing the methane to oxygen ratio the overall conversion of methane actually decreased while the selectivity for $C_2$ compounds increased. This decrease in methane conversion was consistent with the drastic decrease in the amount of $CO_2$ formation when increasing the ratio of methane to oxygen. When the methane-to-oxygen ratio was decreased from about 5:1 to 2:1 at a constant total methane and oxygen pressure, the $CO_2$ formation, the $C_2$ products, and CO yields increased while the formation of ethane remained constant. A further decrease in the methane to oxygen ratio to 1:1 resulted in a large increase in $CO_2$, a small increase in CO, and a small decrease in $C_2$ yield. Thus, it was found that the maximum $C_2$ yield of 18 to 19 percent was obtained over 0.1 $Na_4P_2O_7$/CaO when the methane-to-oxygen ratio was about 2:1. The preferred $C_2$ yield for the 0.5 $Na_4P_2O_7$/$Gd_2O_3$ catalyst of 17 to 18 percent was obtained when the methane oxygen ratio was 2:1. The oxygen conversion when the methane oxygen ratio was 5:1, was very high in the order of about 95 percent.

In order to determine the catalytic function of the catalysts used herein, a comparison of the catalyst 0.1 $Na_4P_2O_7$/CaO was made with a catalyst formed of 0.1 $Na_2CO_3$/CaO so as determine what extent of reactivity the $Na_2P_2O_7$ provides to the catalyst composition. It was found that the $Na_2CO_3$/CaO and the $Na_4P_2O_7$/CaO catalyst tested under similar conditions provided essentially similar $C_2$ yields during initial stages of the reaction. However, it was also found that the $C_2$ yield using the 0.1 $Na_2CO_3$/CaO catalyst during the first 20 hours of the reaction dropped off considerably due to the deactivation of the catalyst to an activity level even below that obtainable with CaO alone. On the other hand, the 0.1 $Na_4P_2O_7$/CaO produced a stable $C_2$ yield during 26 hours of reaction time. A comparison of Na/Ca ratios of these two catalysts indicated that the sodium distributed mainly on the surface of the catalyst containing the $Na_4P_2O_7$ was only slightly decreased during the reaction period. With the catalyst containing the $Na_2CO_3$, there was no significant change in the total sodium even though the surface concentration was drastically changed. Thus, it is believed that the phosphorus appears to have the ability to retain more sodium near the surface of the catalyst for a significantly longer period than that provided by the $Na_2CO_3$, containing catalyst so as to considerably increase the stability of the catalyst.

It will be seen that both the $Na_4P_2O_7$/CaO and $Na_4P_2O_7$/$Gd_2O_3$ catalyst compositions were found to provide active, selective, and stable catalysts for the partial oxidation of methane to higher hydrocarbons with the $C_2$ yields obtained over these catalysts ranging to levels as high as 17 and 19 percent that is expected to be maintainable over extensive reaction durations substantially due to a unique interaction between the sodium and oxide surface. The phosphorus on the surface of the $Na_4P_2O_7$/CaO and $Na_4P_2O_7$/$Gd_2O_3$ was found to stabilize the sodium on the surface of these catalysts without being consumed during the reaction. The major $C_2$ product produced was ethylene and the optimum yield of ethylene was obtained with a methane-to-oxygen ratio of 2:1 for both catalysts. The present catalysts are relatively stable catalysts which are capable for producing high yields of $C_2$ hydrocarbons such as ethane and ethylene from methane over relatively prolonged periods of time so as to provide a viable alternative to the rather expensive and cumbersome technique utilized for the transportation of natural gas to conversion sites.

I claim:

1. A catalyst for facilitating the partial oxidation of methane to $C_2$ hydrocarbons comprising ethane and ethylene in the presence of gaseous oxygen at an elevated temperature, said catalyst consisting of calcium oxide or gadolinium oxide each promoted with sodium pyrophosphate in a concentration of about 0.025 to 0.4 mole per mole of calcium oxide when the catalyst is sodium pyrophosphate/calcium oxide or about 0.1 to 0.7 mole per mole of gadolinium oxide when the catalyst is sodium pyrophosphate/gadolinium oxide.

2. A catalyst as claimed in claim 1, wherein the sodium pyrophosphate content is in the range of about 0.1 to 0.2 mole per mole of calcium oxide.

3. A catalyst as claimed in claim 1, wherein the sodium pyrophosphate is in the range of about 0.5 mole per mole of gadolinium oxide.

4. A method for converting methane to $C_2$ hydrocarbons including ethane and ethylene, consisting of the steps of heating a catalyst consisting of sodium pyrophosphate over calcium oxide or sodium pyrophosphate over gadolinium oxide to a temperature in the range of about 700° to 900° C., and contacting the heated catalyst with a stream of gases comprising methane and oxygen in a methane-to-oxygen ratio in the range of about 1.1 to about 5.1 and at a flow rate sufficient to provide an adequate duration of contact with the catalyst to provide a yield of ethane and ethylene in the range of about 12 to 19 percent.

5. A method for converting methane to $C_2$ hydrocarbons as claimed in claim 4, wherein the catalyst is sodium pyrophosphate/calcium oxide with a sodium pyrophosphate content in the range of about 0.025 to 0.4 mole per mole of calcium oxide.

6. A method for converting methane to $C_2$ hydrocarbons as claimed in claim 4, wherein the catalyst is sodium pyrophosphate/gadolinium oxide with a sodium pyrophosphate content in the range of about 0.1 to 0.7 mole per mole of gadolinium oxide.

7. A method for converting methane to $C_2$ hydrocarbons as claimed in claim 5, wherein the temperature is in the range of about 800° to 850° C., wherein the methane-to-oxygen ratio is about 2:1, and wherein said sodium pyrophosphate content is in a range of about 0.1 to about 0.2 mole per mole of calcium oxide.

8. A method for converting methane to $C_2$ hydrocarbons as claimed in claim 6, wherein the temperature is in the range of about 800° to 850° C., wherein the methane-to-oxygen ratio is about 2:1, and wherein said sodium pyrophosphate content is in a range of about 0.5 mole per mole of gadolinium oxide.

* * * * *